(12) United States Patent
Clay

(10) Patent No.: US 9,242,004 B2
(45) Date of Patent: Jan. 26, 2016

(54) METHODS FOR PREPARING POLYMERS HAVING LOW RESIDUAL MONOMER CONTENT

(71) Applicant: WARSAW ORTHOPEDIC, INC., Warsaw, IN (US)

(72) Inventor: Danielle L. Clay, Collierville, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

(21) Appl. No.: 14/286,673

(22) Filed: May 23, 2014

(65) Prior Publication Data

US 2014/0296449 A1 Oct. 2, 2014

Related U.S. Application Data

(63) Continuation of application No. 13/462,395, filed on May 2, 2012, now Pat. No. 8,735,504.

(51) Int. Cl.
| | |
|---|---|
| C08J 3/00 | (2006.01) |
| A61K 47/34 | (2006.01) |
| C08L 67/04 | (2006.01) |
| C08G 85/00 | (2006.01) |
| B29C 45/00 | (2006.01) |
| A61K 31/4168 | (2006.01) |

(52) U.S. Cl.
CPC .............. *A61K 47/34* (2013.01); *C08G 85/002* (2013.01); *C08J 3/00* (2013.01); *C08L 67/04* (2013.01); *A61K 31/4168* (2013.01); *B29C 45/00* (2013.01); *B29K 2995/006* (2013.01); *C08J 2367/04* (2013.01)

(58) Field of Classification Search
CPC ...... C08G 85/002; B29C 45/00; C08L 67/04; C08J 3/00; C08J 2367/04
USPC .......... 525/410, 411, 415, 450; 528/493, 496, 528/499, 502 A, 502 D
See application file for complete search history.

(56) References Cited

U.S. PATENT DOCUMENTS

| | | | | |
|---|---|---|---|---|
| 4,810,775 | A * | 3/1989 | Bendix et al. ................. | 528/480 |
| 5,342,557 | A * | 8/1994 | Kennedy ........................... | 264/8 |
| 5,759,583 | A | 6/1998 | Iwamoto et al. | |
| 5,942,241 | A | 8/1999 | Chasin et al. | |
| 6,069,129 | A | 5/2000 | Sandberg et al. | |
| 6,179,862 | B1 | 1/2001 | Sawhney | |
| 6,248,345 | B1 | 6/2001 | Goldenheim et al. | |
| 6,287,588 | B1 | 9/2001 | Shih et al. | |
| 6,326,020 | B1 | 12/2001 | Kohane et al. | |
| 6,326,025 | B1 | 12/2001 | Sigler et al. | |
| 6,331,311 | B1 | 12/2001 | Brodbeck et al. | |
| 6,428,804 | B1 | 8/2002 | Suzuki et al. | |
| 6,461,631 | B1 | 10/2002 | Dunn et al. | |
| 6,524,607 | B1 | 2/2003 | Goldenheim et al. | |
| 6,534,081 | B2 | 3/2003 | Goldenheim et al. | |
| 6,589,549 | B2 | 7/2003 | Shih et al. | |
| 6,630,155 | B1 | 10/2003 | Chandrashekar et al. | |
| 6,632,457 | B1 | 10/2003 | Sawhney | |
| 6,773,714 | B2 | 8/2004 | Dunn et al. | |
| 6,921,541 | B2 | 7/2005 | Chasin et al. | |
| 7,287,983 | B2 | 10/2007 | Ilan | |
| 7,727,954 | B2 | 6/2010 | McKay | |
| 7,947,803 | B2 | 5/2011 | Hong et al. | |
| 2002/0009454 | A1 | 1/2002 | Boone et al. | |
| 2002/0090398 | A1 | 7/2002 | Dunn et al. | |
| 2004/0072799 | A1 | 4/2004 | Li et al. | |
| 2004/0082540 | A1 | 4/2004 | Hermida Ochoa | |
| 2004/0109893 | A1 | 6/2004 | Chen et al. | |
| 2004/0214793 | A1 | 10/2004 | Hermida Ochoa | |
| 2004/0219214 | A1 | 11/2004 | Gravett et al. | |
| 2005/0142163 | A1 | 6/2005 | Hunter et al. | |
| 2005/0175709 | A1 | 8/2005 | Baty, III et al. | |
| 2005/0186261 | A1 | 8/2005 | Avelar et al. | |
| 2005/0197293 | A1 | 9/2005 | Mellis et al. | |
| 2005/0288620 | A1 | 12/2005 | Shippert | |
| 2006/0074422 | A1 | 4/2006 | Story et al. | |
| 2006/0104966 | A1 | 5/2006 | Green et al. | |
| 2006/0105026 | A1 | 5/2006 | Fortune et al. | |
| 2006/0148903 | A1 | 7/2006 | Burch et al. | |
| 2006/0153815 | A1 | 7/2006 | Seyda et al. | |
| 2006/0189944 | A1 | 8/2006 | Campbell et al. | |
| 2006/0228391 | A1 | 10/2006 | Seyedin et al. | |
| 2006/0253094 | A1 | 11/2006 | Hadba et al. | |
| 2007/0021358 | A1 | 1/2007 | Edelman et al. | |
| 2007/0066864 | A1 | 3/2007 | Forde | |
| 2007/0104769 | A1 | 5/2007 | Feng et al. | |
| 2007/0156180 | A1 | 7/2007 | Jaax et al. | |
| 2007/0202074 | A1 | 8/2007 | Shalaby | |
| 2007/0224235 | A1 | 9/2007 | Tenney et al. | |
| 2007/0243225 | A1 | 10/2007 | McKay | |
| 2007/0243228 | A1 | 10/2007 | McKay | |
| 2007/0253994 | A1 | 11/2007 | Hildebrand | |
| 2007/0286891 | A1 | 12/2007 | Kettlewell et al. | |
| 2007/0299155 | A1 | 12/2007 | Carpenter et al. | |
| 2008/0009830 | A1 | 1/2008 | Fujimoto et al. | |
| 2008/0038351 | A1 | 2/2008 | Beals et al. | |
| 2008/0039547 | A1 | 2/2008 | Khatri et al. | |
| 2008/0039548 | A1 | 2/2008 | Zavatsky et al. | |

(Continued)

OTHER PUBLICATIONS

Schramm, L.L., et al.; Annual Rep. Prog. Chem., Section C, 2003, vol. 99, p. 3-48.*

(Continued)

*Primary Examiner* — Robert Jones, Jr.
(74) *Attorney, Agent, or Firm* — Sorell Lenna & Schmidt LLP

(57) ABSTRACT

Methods are provided for preparing polymer mixtures having low residual monomer content. The methods comprise mixing the at least two polymers in a solvent to form a polymeric mixture, the polymeric mixture comprising at least one residual monomer; and adding an antisolvent to the polymeric mixture so as to separate the at least two polymers from the polymeric mixture, where the residual monomer is soluble in the antisolvent. In some embodiments, methods are provided for preparing at least two polymers having low residual monomer content, the methods comprise adding an antisolvent to a mixture of at least two polymers dissolved in a solvent so as to precipitate the at least two polymers from the solvent and anti-solvent. The methods provided avoid steps in dry blending of polymers and produces polymer blends that have low residual monomer content.

17 Claims, 1 Drawing Sheet

(56) References Cited

U.S. PATENT DOCUMENTS

| | | |
|---|---|---|
| 2008/0091207 A1 | 4/2008 | Truckai et al. |
| 2008/0096975 A1 | 4/2008 | Guan et al. |
| 2009/0018575 A1 | 1/2009 | Fortune et al. |
| 2009/0030451 A1 | 1/2009 | Hadba et al. |
| 2009/0044895 A1 | 2/2009 | Fortune et al. |
| 2009/0287129 A1 | 11/2009 | Boehringer et al. |
| 2010/0003329 A1 | 1/2010 | Elisseeff |
| 2010/0080838 A1 | 4/2010 | Stopek |
| 2010/0137550 A1 | 6/2010 | Enderle et al. |
| 2010/0173843 A1 | 7/2010 | Hnojewyj |
| 2010/0215659 A1 | 8/2010 | Ladet |
| 2011/0105641 A1 | 5/2011 | Khatri et al. |
| 2011/0111034 A1 | 5/2011 | Wang et al. |

OTHER PUBLICATIONS

Cam, D., et al.; Polymer, 1997, vol. 38, p. 1879-1884.*

You, Y., et al.; Polymer Degradation and Stability, 2005, p. 441-448.*

* cited by examiner

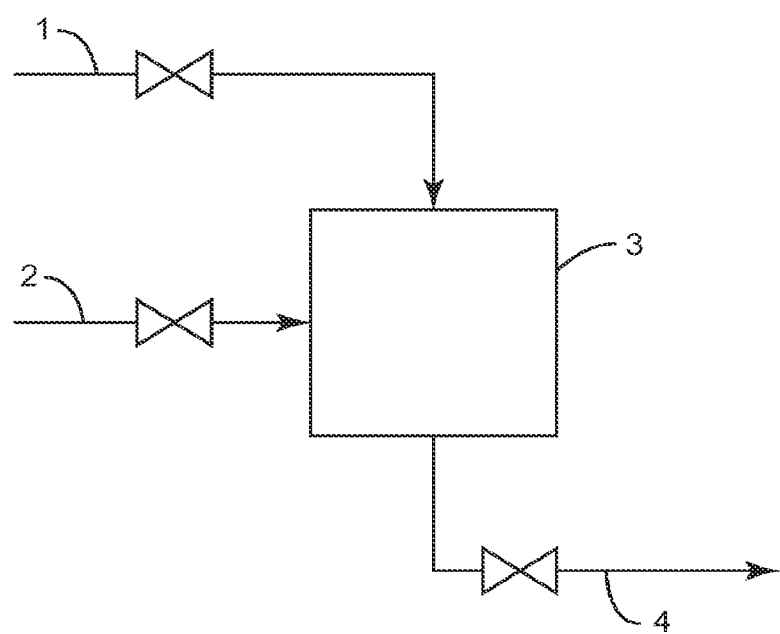

METHODS FOR PREPARING POLYMERS HAVING LOW RESIDUAL MONOMER CONTENT

CROSS-REFERENCE TO RELATED APPLICATION

This application is a continuation of application Ser. No. 13/462,395, filed on May 2, 2012, the contents of which is herein incorporated by reference, in its entirety.

FIELD

This application relates to methods for recovering and purifying polymers and especially for reducing the monomer content of biodegradable polymers.

BACKGROUND

Among various processes of polymerization reactions, solution polymerization process is typically applied to synthesize biodegradable polymers, in which monomers, catalysts, and polymers are all dissolved in a solvent. The reaction begins with the monomers and the catalysts dissolved in a solvent in a reactor. With the activated catalysts the monomers are continuously added to the growing polymer chain at the catalyst active site by coordinate covalent bonding. The dissolution of the polymer in a solvent is maintained to perform the reaction in a single homogeneous liquid phase.

When the reaction is finished, the solution in a reactor becomes a mixture containing the polymer obtained by the synthesis, unreacted monomers, the solvent, and a small amount of catalyst. Accordingly, after the reaction, a process for selectively recovering the polymer from the solution is required.

The presence of monomers in the synthesis of polymers is frequently problematic. For example, in the synthesis of biodegradable polymers such as homopolymers or copolymers based on lactide (L-lactide, D-lactide, DL-lactide, meso-lactide), glycolide, epsilon-caprolactone, dioxanone, trimethylene carbonate, delta-valerolactone, gamma-butyrolactone the presence of monomers is undesirable for various reasons. In many instances monomers decompose more rapidly than biodegradable polymers on exposure to moisture. Consequently, the implantation of monomer-containing biodegradable polymers would therefore lead to a greatly accelerated breakdown of the material in the body. For the same reason, the stability in storage of monomer-containing polymers and implants or pharmaceutical formulations produced therefrom is markedly impaired.

It is well known that drug depots are prepared by well known thermoplastic processes such as melt extrusion or injection molding. The stability of biodegradable polymers is also impaired during thermoplastic processing if residual contents of monomers are present.

In other instances, the encapsulation behavior of non-purified biodegradable polymers is different from that of purified polymers, as are the release behavior and the breakdown behavior. Encapsulated active ingredients, such as peptides, can become damaged or destroyed as a result of the greater amount of free acid present in monomer contaminated polymers compared to purified polymers.

During the synthesis reactions, the residual monomer content of the crude polymer is often difficult to control. Variability in the residual monomer content then automatically also leads to intolerable batch-to-batch variations in the breakdown rate, the stability in storage and the processing stability, so materials of reproducible quality cannot be obtained without a subsequent purification step to reduce the amount of residual monomers.

It would therefore be desirable to develop improved polymer recovery and purification methods that minimize the presence of monomers in melt extrudable polymers and at the same time reduce the number of unit operations required to produce the same thereby reducing both the time and cost of manufacturing.

SUMMARY

Methods are provided for recovering at least two polymers including dissolving the at least two polymers in a solvent to form a polymeric mixture which also includes at least a monomer. An antisolvent, which is a solvent for the monomer but not a solvent for the at least two polymers, is then added to the polymeric mixture and the at least two polymers precipitate out of the polymeric solution. In this way, the precipitated product has low residual monomer content.

The at least two polymers present in the precipitate are then separated from the remaining monomeric solution by decanting, centrifugation, microfiltration, ultrafiltration, sieving or a combination thereof. Once formed the precipitate including the at least two polymers can be dried by evaporation with air or nitrogen or freeze-drying.

The polymeric mixture containing the at least two polymers can be homogenous and form a polymeric solution in which the at least two polymers have similar solubilities in the solvent.

In some embodiments the at least two polymers recovered according to methods of the present disclosure comprise, consist essentially of, or consist of biodegradable polymers selected from polylactide (PLA) or one or more of poly(lactide-co-glycolide) (PLGA), polylactide (PLA), polyglycolide (PGA), D-lactide, D,L-lactide, L-lactide, L-lactide-co-ε-caprolactone, D,L-lactide-co-ε-caprolactone, D,L-lactide-co-glycolide-co-ε-caprolactone, poly (D,L-lactide-co-caprolactone), poly (L-lactide-co-caprolactone), or a combination thereof. In other embodiments, the at least two polymers comprise, consist essentially of, or consist of poly (lactic-co-glycolide) and said poly(lactic-co-glycolide) comprises a mixture of polyglycolide and polylactide. In yet other embodiments, the at least two polymers present in the polymeric mixture comprise, consist essentially of, or consist of more polylactide than polyglycolide.

In some embodiments, the at least two polymers are derived from one or more monomers selected from lactide (L-lactide, D-lactide, DL-lactide, meso-lactide), glycolide, trimethylene carbonate, epsilon-caprolactone, gamma-butyrolactone, dioxanone, delta-valerolactone, polymerisable heterocycles or polyethylene glycols.

Solvents capable of dissolving the at least two polymers include without limitation n-hexane, cyclohexane, heptanes, methylene chloride, ethyl acetate, acetone, polyethylene glycols as esters or ethers, polyethoxylated fatty acids, hydroxylated fatty acids, fatty alcohols, polyethoxylated castor oil, polyethoxylated hydrogenated castor oil, polyethoxylated fatty acid from castor oil, polyethoxylated fatty acid from hydrogenated castor oil, Cremophor, Myrj, Polyoxyl 40 stearate, Emerest 2675, Lipal 395, Tween, Span and HCO 50, glycerin, N,N-dimethylacetamide, ethyl alcohol, denatured alcohol, ester, acetone, transcutol or a combination thereof. Useful antisolvents serve as solvents for the monomer but are non-solvents for the at least two polymers and include without limitation water, ethanol, methanol, supercritical carbon dioxide, supercritical nitrogen, supercritical water or mixtures thereof.

In some embodiments, it is contemplated that the polymeric mixture includes more than two polymers, for example, a first polymer in an amount of about 10%, a second polymer in an amount of about 20%, a third polymer in an amount of about 50% and a fourth polymer of about 20%.

In some embodiments, the methods provided avoid or limit the dry blending steps when blending polymers and/or co-polymers.

In another embodiment, methods are provided for recovering at least two polymers comprising, consisting essentially of, or consisting of dissolving the at least two polymers in a solvent to form a polymeric mixture, adding an antisolvent to the polymeric mixture to form a precipitate of the at least two recovered polymers and separating the at least two recovered polymers from the remaining monomeric solution. The polymeric mixture includes a monomer and the antisolvent is a solvent for the monomer and a non-solvent for the at least two polymers.

In other embodiments, the at least two biodegradable polymers recovered according to methods described in this disclosure are useful in the manufacture of drug depots especially by hot melt extrusion. Drug depots manufactured from the at least two polymers recovered and/or purified according to methods described in this disclosure: (i) consist of only the active pharmaceutical ingredient (or one or more of its pharmaceutically acceptable salts) and the biodegradable polymer(s); or (ii) consist essentially of the active pharmaceutical ingredient (and/or one or more of its pharmaceutically acceptable salts) and the biodegradable polymer(s); or (iii) comprise the active pharmaceutical ingredient (and/or one or more of its pharmaceutically acceptable salts), and the biodegradable polymer(s) and one or more other active ingredients, surfactants, excipients or other ingredients or combinations thereof. When there are other active ingredients, surfactants, excipients or other ingredients or combinations thereof in the formulation, in some embodiments these other compounds or combinations thereof comprise less than 50 wt. %. less than 40 wt. %, less than 30 wt. %, less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. %.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

Reference will now be made in detail to certain embodiments of the invention. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

BRIEF DESCRIPTION OF THE DRAWING

In part, other aspects, features, benefits and advantages of the embodiments will be apparent with regard to the following description, appended claims and accompanying drawing where:

FIG. 1 is a schematic of the process in accordance with the principles of the present disclosure.

It is to be understood that the FIGURE are not drawn to scale. Further, the relation between objects in a FIGURE may not be to scale, and may in fact have a reverse relationship as to size. The FIGURE is intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

DEFINITIONS

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Generally, the term "biodegradable polymer" means a synthetic or a naturally derived biodegradable, biocompatible polymer that may be absorbed (resorbed) once implanted in a living mammalian body. In the present application biodegradable polymer refers to synthetically derived polymers. Synthetic biodegradable polymers include, but are not limited to, polyethylene glycol (PEG), polyvinyl alcohol (PVA), polyorthoester (POE), polylactic acid (PLA), polyglycolic acid (PGA), polyactic-glycolic acid (PLGA) and combinations thereof.

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. In some embodiments, the drug depot has a modulus of elasticity in the range of about $1\times10^2$ to about $6\times10^5$ dyn/cm$^2$, or $2\times10^4$ to about $5\times10^5$ dyn/cm$^2$, or $5\times10^4$ to about $5\times10^5$ dyn/cm$^2$. In some embodiments, the drug depot is in solid form and comprises the mixed monoamine reuptake inhibitor.

A "drug depot" is the composition in which a drug or active pharmaceutical ingredient is administered to the body. Thus, a drug depot may comprise a physical structure to facilitate implantation and retention in a desired site (e.g., a disc space, a spinal canal, a tissue of the patient, particularly at or near a site of chronic pain, etc.). The drug depot may also comprise the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.01 cm to about 20 cm from the administration site and comprises the active pharmaceutical ingredient. A drug depot may also include a pump or pellet.

A "therapeutically effective amount" or "effective amount" is such that when administered, the drug results in alteration of the biological activity, such as, for example, inhibition of inflammation, reduction or alleviation of pain or spasticity, improvement in the condition through muscle relaxation, etc. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

The term "biodegradable" includes that all or parts of the drug depot will degrade over time by the action of enzymes, by hydrolytic action and/or by other similar mechanisms in the human body. In various embodiments, "biodegradable" includes that the depot (e.g., microparticle, microsphere, etc.) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The phrases "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s).

The two types of formulations (sustain release and immediate release) may be used in conjunction. The sustained release and immediate release may be in one or more of the same depots. In various embodiments, the sustained release and immediate release may be part of separate depots. For example a bolus or immediate release formulation of an active pharmaceutical ingredient may be placed at or near the target site and a sustain release formulation may also be placed at or near the same site. Thus, even after the bolus becomes completely accessible, the sustain release formulation would continue to provide the active ingredient for the intended tissue.

In various embodiments, the drug depot can be designed to cause an initial burst dose of therapeutic agent within the first twenty-four to seventy-two hours after implantation. "Initial burst" or "burst effect" or "bolus dose" refers to the release of therapeutic agent from the depot during the first twenty-four hours to seventy-two hours after the depot comes in contact with an aqueous fluid (e.g., synovial fluid, cerebral spinal fluid, etc.). In some embodiments, the steroid can also be administered in a bolus dose. The "burst effect" is believed to be due to the increased release of therapeutic agent from the depot. In alternative embodiments, the depot (e.g., gel) is designed to avoid or reduce this initial burst effect (e.g., by applying an outer polymer coating to the depot).

The term "implantable" as utilized herein refers to a biocompatible device (e.g., drug depot) retaining potential for successful placement within a mammal. The expression "implantable device" and expressions of the like import as utilized herein refers to an object implantable through surgery, injection, or other suitable means whose primary function is achieved either through its physical presence or mechanical properties.

"Localized" delivery includes delivery where one or more drugs are deposited within a tissue, for example, a nerve root of the nervous system or a region of the brain, or in close proximity (within about 0.1 cm, or preferably within about 10 cm, for example) thereto. For example, the drug dose delivered locally from the drug depot may be, for example, 10%, 20%, 30%, 40%, 50%, 60%, 70%, 80%, 90%, 95%, 99%, 99.9% or 99.999% less than the oral dosage or injectable dose. In turn, systemic side effects, such as for example, liver transaminase elevations, hepatitis, liver failure, myopathy, constipation, etc. may be reduced or eliminated. In some embodiments, the depot is not to be administered at or near the eye.

The term "mammal" refers to organisms from the taxonomy class "mammalian," including but not limited to humans, other primates such as chimpanzees, apes, orangutans and monkeys, rats, mice, cats, dogs, cows, horses, etc.

"Targeted delivery system" provides delivery of one or more drugs depots, gels or depots dispersed in the gel having a quantity of therapeutic agent that can be deposited at or near the target site as needed for treatment of pain, inflammation or other disease or condition.

The abbreviation "DLG" refers to poly(DL-lactide-co-glycolide).

The abbreviation "DL" refers to poly(DL-lactide).

The abbreviation "LG" refers to poly(L-lactide-co-glycolide).

The abbreviation "CL" refers to polycaprolactone.

The abbreviation "DLCL" refers to poly(DL-lactide-co-caprolactone).

The abbreviation "LCL" refers to poly(L-lactide-co-caprolactone).

The abbreviation "G" refers to polyglycolide.

The abbreviation "PEG" refers to poly(ethylene glycol).

The abbreviation "PGA" refers to polyglycolic acid.

The abbreviation "PLGA" refers to poly(lactide-co-glycolide) also known as poly(lactic-co-glycolic acid), which are used interchangeably.

The abbreviation "PLA" refers to polylactide.

The abbreviation "POE" refers to poly(orthoester).

The abbreviation "PVA refers to polyvinyl alcohol.

Biodegradable polymers useful in the preparation of drug depots can be easily hot melt extrudable. In order to produce hot melt extrudable polymers many processes include three unit operations, (i) milling or grinding to reduce polymer particle size; (ii) homogenous blending when more than one polymer is used; and (iii) reduction of the residual monomer. The presence of monomers in biodegradable polymers interferes with the melt extrusion process and results in the production of unstable drug depots. It has now been surprisingly found that according to the recovery and purification methods provided in this application, biodegradable polymers having an insignificant amount of monomers can be provided. The purification methods of this application provide a unique way of homogeneously mixing at least two or more polymers with similar solubilities while also combining three unit operations into a single processing step to reduce both time and cost of manufacturing.

In some embodiments a method for recovering at least two polymers having similar solubilities is provided, the method including dissolving the at least two or more polymers in a solvent to form a polymeric mixture, which mixture contains at least a monomer; adding an antisolvent in which the monomer is solvent but which is a non-solvent or ant-solvent for the at least two polymers to the polymeric mixture so as to form a precipitate of the at least two polymers and a monomeric solution containing at least one monomer. The precipitate of the at least two polymers is subsequently recovered from the monomeric solution to provide polymers of high purity. The process described in this disclosure is particularly useful to produce biodegradable polymers of high purity useful in the manufacture of drug depots by hot melt extrusion.

It will be understood by those of ordinary skill in the art that the solvent is the substance that the polymer is able to dissolve in. The polymer is soluble in the solvent. However, when an anti-solvent is introduced for the polymer, the monomer is soluble in the anti-solvent for the polymer. Because the polymer is not soluble or insoluble in the anti-solvent, the polymer will precipitate out of the liquid and there can be highly pure polymer or blends of polymer recovered in a product. This product can be used to make the medical device (e.g., drug depot).

In some embodiments, the solubility range of the polymer in the solvent is greater than from about 0.5 mg/ml to greater than about 2 mg/ml or greater than 1 mg/ml. In some embodiments, the polymer is insoluble in the solvent when it is less than 0.1 mg/ml, for example from about 0.05 mg/ml to about 0.01 mg/ml.

In various embodiments, the polymer particle size used is from about 5 to 500 micrometers, however, in various embodiments ranges from about 10 micron to 350 microns may be used. In some embodiments, the polymer particle size range comprises from about 25 micrometer to about 300 micrometers. In some embodiments, the polymer particle size range comprises from about 50 micrometer to about 200 micrometers.

An example of an embodiment of the method described in this disclosure is set forth in FIG. 1, wherein 1 represents the inflow of at least two polymers into the reaction vessel 3, while 2 is the inflow of the antisolvent to the reaction vessel 3 and 4 represents the outflow of a precipitate of the at least two polymers after separation from the reaction vessel 3. FIG. 1 shows a unique way of homogeneously mixing at least two or more polymers with similar solubilities which process efficiently and economically combines the unit operations of particle size reduction and residual monomer removal into a single step.

In some embodiments, the moist precipitate of at least two polymers is separated effectively by means of gravity and subsequently the precipitate can be dried by evaporation with air, nitrogen or freeze-drying. Other means of separation of the precipitate containing the at least two polymers and the monomeric solution include decanting, centrifugation, microfiltration, ultrafiltration, sonication, sieving or a combination thereof. After the drying, the solvent and/or moisture content of the at least two biodegradable polymers is less than 2%, values of below 1%, in particular values of below 0.5% and less than 0.1% being achieved under beneficial settings.

The at least two polymers that can be purified according to the methods provided herein include without limitations (i) polylactide (PLA) or (ii) one or more of poly(lactide-co-glycolide) (PLGA), polylactide (PLA), polyglycolide (PGA), D-lactide, D,L-lactide, L-lactide, L-lactide-co-ϵ-caprolactone, D,L-lactide-co-ϵ-caprolactone, D,L-lactide-co-glycolide-co-ϵ-caprolactone, poly(D,L-lactide), poly(L-lactide), poly (D-L-lactide-co-caprolactone), poly (L-lactide-co-caprolactone) or a combination thereof.

In other aspects, the at least two polymers contain one or more units derived from lactide (L-lactide, D-lactide, D,L-lactide, meso-lactide), glycolide, trimethylene carbonate, epsilon-caprolactone, gamma-butyrolactone, dioxanone, delta-valerolactone and/or similar polymerisable heterocycles and/or polyethylene glycols. Particularly preferred are polymers composed of D,L-lactide or copolymers of D,L-lactide and glycolide having any desired composition or a block copolymer of D,L-lactide, or D,L-lactide-co-glycolide having any desired composition and polyethylene glycol.

In yet other embodiments, the at least two biodegradable polymers include a mixture of polyglycolide and polylactide. In other embodiments the polymeric mixture resulting from dissolving the at least two polymers includes more polylactide than polyglycolide.

In various embodiments, the at least two polymers are polymer gels prepared by copolymerizing monomers including (meth)acrylic acid, (meth)acrylamide, N-substituted (meth)acrylamides and unsaturated carboxylic acid.

In other embodiments, the method described in this application can be utilized to purify cyclic olefin polymers whose monomers typically show very high boiling point temperature (150° C. or more) and polymers not having a specific melting point temperature. Cyclic olefin copolymers are produced by chain copolymerization of cyclic monomers such as 8,9,10-trinorborn-2-ene (norbornene) or 1,2,3,4,4a,5,8,8a-octahydro-1,4:5,8-dimethanonaphthalene (tetracyclododecene) with ethene.

While the purifying method requires the homogeneous mixing of at least two polymers, other polymeric combinations are also contemplated. For example, a blend of biodegradable polymers includes a first polymer in an amount of about 10%, a second polymer in an amount of about 20%, a third polymer in an amount of about 50% and a fourth polymer of about 20%.

The at least two polymers are homogeneously mixed by dissolving them into a solvent in which the at least two polymers are soluble and preferably have similar solubilities, thereby forming a polymeric mixture, which in some embodiments can be a polymeric solution. In the polymeric mixture the at least two polymers mix at molecular level.

Useful solvents for dissolving the at least two polymers include without limitations n-hexane, cyclohexane, heptanes, methylene chloride, ethyl acetate, acetone or combinations thereof. For effective recovery or purification of the at least two polymers, it is preferable that the monomers still present in the polymeric mixture are insoluble in the solvents utilized to dissolve the at least two polymers. However, in order to purify effectively the at least two polymers, the monomers still present in the polymeric mixture must be soluble in an antisolvent, which when added to the polymeric solution causes the precipitation of the at least two polymers.

Suitable antisolvents include without limitation water, ethanol, methanol or combinations thereof. Water as the antisolvent is particularly effective since it is non-toxic, non-explosive, cost-effective and environmentally acceptable. In some embodiments, the solvent comprises supercritical water, supercritical carbon dioxide, super critical nitrogen or a combination thereof.

The at least two polymers are recovered from the polymeric mixture obtained after polymerization by using a precipitation phenomenon that a polymer dissolved in a solvent precipitates out in a solid form when the antisolvent having a very low solubility of polymer is added to the polymeric mixture. The precipitation phenomenon means that when an antisolvent is added to a polymer material dissolved in a liquid by a solvent, when the anti-solvent is added which cannot dissolve the polymer material, but can dissolve the monomer, the polymer material is precipitated out in a solid form. The antisolvent is a material, which can be mixed with the solvent of the polymer mixture but is a non-solvent with respect to the polymer material to be separated. The monomer that is contained in the polymer is, however, soluble in the antisolvent. If the antisolvent is used in a sufficiently large amount, the polymer material is precipitated while coming into contact with the antisolvent. Accordingly, the precipitation phenomenon relates to a phase-conversion reaction where the liquid polymer phase is rapidly converted into solid phase. However, the monomer will remain in the mixture.

With respect to the at least two polymers present in the polymeric mixture, the precipitation phenomenon is used in order to recover the at least two polymers in the polymer mixture synthesized after the polymerization reaction. A batch type dropping method can be used to facilitate the precipitation phenomenon. Examples of the dropping method may include a forward dropping method where a polymerization mixture is added to an antisolvent as a liquid droplet, and a backward dropping method where an antisolvent is added to a polymerization solution as a liquid droplet. In a polymerization process of biodegradable polymers, the above-mentioned dropping precipitation method is used and a single kind of antisolvent for complete precipitation or two kinds of antisolvents for partial precipitation followed by complete precipitation are used to perform the process. The reason why two or more kinds of antisolvents are used during the dropping method is that it is easy to obtain the polymer in a particle form as compared to the case of a single kind of antisolvent. First, the antisolvent for partial precipitation is added to the polymerization mixture to partially precipitate the polymer. At this time, the polymerization mixture is changed from a clear and transparent liquid state to a semi-transparent and frosty state. Next, a large amount of antisolvent for complete precipitation is added to completely precipitate the polymer particles. The at least two polymers which are dissolved in the polymerization mixture are precipitated out in a solid form if the antisolvent is added thereto. In respect to the dropping method, very small solid particles are first formed during the partial precipitation, and the formed solid particles coagulate to each other to form larger size particles when the antisolvent for complete precipitation is further added. In this case, it is presumed that the particle size is determined depending on the supply rate of the antisolvent and the rpm of an impeller in a precipitation reactor or the tip speed of the impeller. A repulsive force against a cohesive force between particles is generated due to a shearing force from the impeller. Accordingly, if the cohesive force between particles is larger than the repulsive force generated due to the shearing force of the impeller, the particle size will be continuously increased. Meanwhile, as the precipitation of particles reaches the complete precipitation, the cohesive force between particles is decreased. When particles have been completely precipitated, the cohesive force is hardly generated between particles since salvation effect by solvent is blocked by antisolvent.

In a dropping method, however, an antisolvent is gradually supplied onto the surface of a polymer solution, while high shearing force is generated near the impeller and a relatively low shearing force is generated on the surface of the solution. Therefore, if particles are strongly cohered on the surface of the solution, there is a possibility that the polymer is obtained in the form of not particles but a cake.

In some embodiments, the temperature, pH, and other characteristics of the solvent and antisolvent can be used to optimize the purification process described herein. For example, maintaining the polymeric mixture at a temperature from about 15° C. to about 100° C. increases the rate of dissolution. Similarly, adding the antisolvent at a temperature from about 15° C. to about 100° C. accelerates the formation of a precipitate containing the at least two polymers or polymer blends with copolymers. The process of this application also contemplates adjusting the pH of the polymeric mixture and/or the monomeric solution to optimize the conditions under which the at least two polymers are recovered. For example, maintaining the polymeric mixture at a pH of 4-6 enhances the dissolution of the at least two polymers. Similarly, maintaining the pH of the antisolvent at a pH of about 7 enhances the solubility of the monomers and accelerates the precipitation process.

In some embodiments, in order to increase the molecular dispersion of the raw biodegradable polymers, other ingredients can be added to the polymeric solution, such as for example, other co-solvents, wetting agents and dispersants. In various embodiments, dispersants can include gas such as carbon dioxide or surfactants.

Useful surfactants include anionic, cationic, amphoteric, non-ionic surfactants or combinations thereof. A non-limiting list of surfactants which may be used in accordance with the methods described herein include long-alkyl-chain sulfonates, alkyl aryl sulfonates, dialkyl sodium sulfosuccinates, alkyl sulfates, quaternary ammonium salts, fatty alcohols such as lauryl, cetyl and stearyl alcohols; glyceryl esters such as mono-, di- and triglycerides; and fatty acid esters of fatty alcohols and other alcohols such as propylene glycol, polyethylene glycol, sorbitan, sucrose and cholesterol; polyoxyethylene glyceryl, steroidal esters, polyoxypropylene esters, and combinations thereof.

After the at least two polymers are recovered and purification has been carried out using the methods according this application, a residual monomer content of less than 1%, preferably less than 0.5%, most preferably less than 0.1% can be achieved.

The polymers, before the method is performed, comprise one or more monomeric units (e.g., monomers, dimmers, trimers, tetramers, pentamers, hexamers, or other small oligomers) that are not part of the polymer chain, however, the monomer interacts with the polymer chain and represents monomeric impurities. An impurity in the polymer, includes, but is not limited to an unintended constituent present in the manufactured polymer substance. It may, in some embodiments, originate from the starting materials, such as the monomers, or other reactants, or be the result of secondary or incomplete reactions during the production process such as oligomers. While it is present in the polymer it was not intentionally added. Examples of such impurities in a polymer include unreacted monomers, monomer intermediates, other reactants, oligomers, residual polymerization catalysts, or other contaminants from the manufacturing process. These unreacted or residual monomers can be associated with the polymer.

The recovered polymer, or polymer blend after it is recovered is substantially pure, which means that the polymer is substantially free from residual monomer content. In various embodiments, the polymer is at least 95% free, at least 99% free, at least 99.5% free or at least 99.9% free of residual monomer materials. Polymer is considered to be substantially pure if it is at least 95%, at least 99%, at least 99.5%, at least 99.9% free from residual monomer material. Therefore, there is a low residual levels of monomer content of less than 5%, less than 2.5%, less than 1%, less than 0.5%, or less than 0.1% w/w, w/v, or v/v in the polymer.

As a result of the methods described herein, the recovered at least two polymers have smaller polymer domain. For example, while the non-purified polymers contain polymer domains of more than 1 cm, the recovered, purified polymers have polymer domains of less than 0.1 mm, preferably less than 0.05 mm, most preferably less than 0.025 mm. In some embodiments, if you mix the at least two polymers using a dry blending technique, the domain size would be similar to the starting particle size. In this case, you can have domain sizes that are on the order of a molecular dispersion of the polymers In some embodiments, the polymers recovered utilizing the methods of the present application are a free flowing powder having a smaller particle size than the non-purified polymers. For example, the raw, at least two polymer mixture can have a particle size from about 400 µm to about 1000 µm, from about 500 µm to about 2000 or from about 1000-4000 µm while the recovered polymers have a particle size from about 25 µm to about 300 µm. In various embodiments, the recovered biodegradable polymer particle size, which may be in powdered form is from about 5 to 30 micrometers. In some embodiments, the polymer can be obtained a pellet with dimension of from about 0.5-2.0 mm diameter to and about 1-6 mm length.

In some embodiments, at least 75% of the particles of the polymer have a size from about 10 micrometer to about 300 micrometers. In some embodiments, at least 85% of the particles have a size from about 10 micrometer to about 300 micrometers. In some embodiments, at least 95% of the particles have a size from about 10 micrometer to about 300 micrometers. In some embodiments, all of the particles have a size from about 10 micrometer to about 300 micrometers.

In some embodiments, at least 75% of the particles of the recovered biodegradable polymers have a size from about 20 micrometer to about 180 micrometers. In some embodiments, at least 85% of the particles have a size from about 20 micrometers to about 180 micrometers. In some embodiments, at least 95% of the particles have a size from about 20 micrometer to about 180 micrometers. In some embodiments, all of the particles of the recovered biodegradable polymers have a size from about 20 micrometer to about 180 micrometers. In some embodiments, at least 80% of the particles have a size from 5 microns to about 100 microns on a volume basis.

The biodegradable polymers recovered according to the methods described herein can be subjected to hot-melt extrusion, spray drying, injection molding to be shaped into a variety of shapes such as microparticles, nanoparticles and the like. A particularly preferred use of the recovered biodegradable polymers provides for the production of pharmaceutical formulations or resorbable implants, such as, for example, drug depots.

In various embodiments, a drug depot manufactured from biodegradable polymers selected from the at least two polymers recovered and purified according to methods described in this disclosure include, for example, poly(lactide-co-glycolide) (PLGA), polylactide (PLA), polyglycolide (PGA), D-lactide, D,L-lactide, L-lactide, D,L-lactide-co-ϵ-caprolactone, D,L-lactide-co-glycolide-co-ϵ-caprolactone or copolymers thereof or a combination thereof.

In some embodiments, the drug depot comprises one or more polymers (e.g., PLA, PLGA, etc.) having a MW of from about 15,000 to about 150,000 Da or from about 25,000 to about 100,000 Da. In some embodiments, the drug depot comprises one or more polymers (poly (D-lactide) caprolactone, etc.) having an inherent viscosity of 0.6 to about 1.0 dL/gm and a MW of 50,000 to about 125,000 Da, or from 50,000 to about 70,000 Da.

As persons of ordinary skill in the art are aware, an implantable depot compositions having a blend of polymers with different end groups are used the resulting formulation will have a lower burst index and a regulated duration of delivery. For example, one may use polymers with acid (e.g., carboxylic acid) and ester end groups (e.g., methyl or ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower initial burst and a regulated duration of delivery.

In various embodiments, the polymer may have a pre-dosed viscosity in the range of about 1 to about 2000 centipoise (cps), 1 to about 200 cps, or 1 to about 100 cps. The depot may have a modulus of elasticity in the range of about $1 \times -10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In various embodiments, the polymer used in the depot has a molecular weight, as shown by the inherent viscosity, from about 0.10 dL/g to about 1.2 dL/g or from about 0.10 dL/g to about 0.40 dL/g. Other IV ranges of the polymers in the depot include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.50 dL/g, about 0.50 to about 0.70 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, and about 1.8 to about 2.1 dL/g.

In some embodiments, the drug depot is solid and has a modulus of elasticity in the range of about $1 \times -10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. If the depot is to be placed in the spinal area, in various embodiments, the depot may comprise sterile preservative free material.

In a depot the active drug may also be administered with non-active ingredients. These non-active ingredients may have multi-functional purposes including the carrying, stabilizing and controlling the release of the therapeutic agent(s). The sustained release process, for example, may be by a solution-diffusion mechanism or it may be governed by an erosion-sustained process. Typically, the depot will be a solid or semi-solid formulation comprised of a biocompatible material that can be biodegradable.

Exemplary excipients that may be formulated with an active pharmaceutical ingredient in addition to the biodegradable polymer include but are not limited to MgO (e.g., 1 wt. %), mPEG, TBO-Ac, PEG, Span-65, Span-85, pluronic F127, sorbitol, cyclodextrin, maltodextrin, pluronic F68, CaCl$_2$, trehalose, mannitol, dextran, and combinations thereof. In some embodiments, the excipients comprise from about 0.001 wt. % to about 50 wt. % of the formulation. In some embodiments, the excipients comprise from about 0.001 wt. % to about 40 wt. % of the formulation. In some embodiments, the excipients comprise from about 0.001 wt. % to about 30 wt. % of the formulation. In some embodiments, the excipients comprise from about 0.001 wt. % to about 20 wt. % of the formulation. In some embodiments, the excipients comprise from about 0.001 wt. % to about 10 wt. % of the formulation. In some embodiments, the excipients comprise from about 0.001 wt. % to about 5 wt. % of the formulation. In some embodiments, the excipients comprise from about 0.001 wt. % to about 2 wt. % of the formulation.

In various embodiments, the non-active ingredients will be durable within the tissue site for a period of time equal to or greater than (for biodegradable components) or greater than (for non-biodegradable components) the planned period of drug delivery.

In some embodiments, the depot material may have a melting point or glass transition temperature close to or higher than body temperature, but lower than the decomposition or degradation temperature of the therapeutic agent. In some embodiments, a plasticizer is used to lower the glass translation temperature in order to affect the stability of the drug depot. However, the pre-determined erosion of the depot material can also be used to provide for slow release of the loaded therapeutic agent(s). Non-biodegradable polymers include but are not limited to PVC and polyurethane.

In some embodiments, the drug depot may not be fully biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics, methacrylates, poly (N-isopropylacrylamide), PEO-PPO-PEO (pluronics) or combinations thereof. Typically, these types of drug depots may need to be removed after a certain amount of time.

In some instances, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

In various embodiments, the depot may comprise a bioerodible, a bioabsorbable, and/or a biodegradable biopolymer that may provide immediate release, or sustained release of the drug. Examples of suitable sustained release biopolymers include but are not limited to polymers recovered and purified according to methods described in this application such as poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ε-caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations. In some embodiments, these biopolymers may also be coated on the drug depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the drug from the depot. In some embodiments, the range of the coating on the drug depot ranges from about 5 microns to about 250 microns or 5 microns to about 200 microns to delay release from the drug depot.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film or sheet (e.g., ribbon-like) or the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 4 mm. In various embodiments, as the diameter decreases, the surface area that comes in contact with the bodily fluid of the depot increases and therefore release of the drug from the depot increases. In various embodiments, the drug depot may have a layer thickness of from about 0.005 to 1.0 mm, such as, for example, from 0.05 to 0.75 mm.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, bismuth, iodine, tantalum, tungsten, and/or metal beads or particles. In various embodiments, the radiographic marker could be a spherical shape or a ring around the depot.

Gel

The at least two polymers recovered and/or purified according to methods described herein are also useful to form drug delivery systems comprising or comprised into a drug depot.

In one embodiment, a depot comprises an adherent gel comprising an active pharmaceutical ingredient that is evenly distributed throughout a gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided that hardens or stiffens after delivery. Typically, hardening gel formulations may have a pre-dosed modulus of elasticity in the range of about $1 \times -10^2$ to about $3 \times 10^5$ dynes/cm$^2$, or $2 \times 10^4$ to about $2 \times 10^5$ dynes/cm$^2$, or $5 \times 10^4$ to about $1 \times 10^5$ dynes/cm$^2$. The post-dosed hardening gels (after delivery) may have a rubbery consistency and have a modulus of elasticity in the range of about $1 \times -10^2$ to about $2 \times 10^6$ dynes/cm$^2$, or $1 \times 10^5$ to about $7 \times 10^5$ dynes/cm$^2$, or $2 \times 10^5$ to about $5 \times 10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances. In some embodiments, the polymer comprises 20 wt. % to 90 wt. % of the formulation.

In various embodiments, the molecular weight of the gel can be varied by many methods known in the art. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, incorporation of chain transfer or chain capping agents and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel that includes a high molecular weight polymer tends to coagulate or solidify more quickly than a polymeric composition that includes a low-molecular weight polymer. Polymeric gel formulations that include high molecular weight polymers, also tend to have a higher solution viscosity than a polymeric gel that includes low-molecular weight polymers. In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000 g/mol.

When the gel is designed to be a flowable gel, it can vary from low viscosity, similar to that of water, to high viscosity, similar to that of a paste, depending on the molecular weight and concentration of the polymer used in the gel. The viscosity of the gel can be varied such that the polymeric composition can be applied to a patient's tissues by any convenient technique, for example, by brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and may have a longer degradation time). Typically, when the polymers have similar components but different MWs, a gel with a high molecular weight provides a stronger matrix and the matrix takes more time to degrade. In contrast, a gel with a low molecular weight degrades more quickly and provides a softer matrix. In various embodiments, the gel has a molecular weight, as shown by the inherent viscosity, from about 0.10 dL/g to about 1.2 dL/g or from about 0.10 dL/g to about 0.40 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, and about 1.8 to about 2.1 dL/g.

In some embodiments, when the polymer materials have different chemistries (e.g., high MW DLG 5050 and low MW DL), the high MW polymer may degrade faster than the low MW polymer.

In various embodiments, the gel can have a viscosity of about 300 to about 5,000 centipoise (cp). In other embodiments, the gel can have a viscosity of from about 5 to about 300 cps, from about 10 cps to about 50 cps, or from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly(methoxyethoxy-ethyl-methacrylate), polymethyl-methacrylate (PMMA), methylmethacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly (N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyetherurethane, or a combination thereof.

In some embodiments there is a method for making an implantable drug depot. The method may comprise combining a biocompatible polymer recovered according to methods described in this application and a therapeutically effective amount of active pharmaceutical ingredient or a pharmaceutically acceptable salt thereof and forming the implantable drug depot from the combination.

In various embodiments, the drug depot comprising the active pharmaceutical ingredient can be made by combining a biocompatible polymer and a therapeutically effective amount of active pharmaceutical ingredient or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, lubricious layers, and so forth can be formed. If desired, the solution can further comprise, one or more of the following: an active pharmaceutical ingredient and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: an active pharmaceutical ingredient, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, the active pharmaceutical ingredient may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear, in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of the therapeutic agent because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion process may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., pellet) is cooled. Examples of cooling processes include air cooling and/or immersion in a cooling bath. In some embodiments, a water bath is used to cool the extruded depot. However, where a water-soluble therapeutic agent such is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired. In some embodiments, the drug depot has a burst release surface that releases about 10%, 15%, 20%, 25%, 30%, 35%, 45%, to about 50% of the drug over 24 or 48 hours.

In various embodiments, the drug depot can be prepared by mixing or spraying the drug with the polymer and then molding the depot to the desired shape. In various embodiments, an active pharmaceutical ingredient is used and mixed or sprayed with the PLGA or PEG550 polymer, and the resulting depot may be formed by extrusion and dried.

In some embodiments, the drug depot comprises the at least two biodegradable polymers recovered and/or purified according to methods described herein in a wt % of about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the depot and the remainder is active and/or inactive pharmaceutical ingredients.

In some embodiments, the at least two biodegradable polymers recovered according to methods described in this application comprise poly(lactic-co-glycolide) (PLGA) or poly(orthoester) (POE) or a combination thereof. The poly(lactic-co-glycolide) may comprise a mixture of polyglycolide (PGA) and polylactide and in some embodiments, in the mixture, there is more polylactide than polyglycolide. In various embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer is polyglycolide.

In various embodiments, the drug particle size, which may be in powdered form, is from about 5 to 30 micrometers, however, in various embodiments ranges from about 1 micron to 250 microns may be used. In some embodiments, the biodegradable polymer comprises at least 50 wt. %, at least 60 wt. %, at least 70 wt. %, at least 80 wt. % of the formulation, at least 85 wt. % of the formulation, at least 90 wt. % of the formulation, at least 95 wt. % of the formulation or at least 97 wt. % of the formulation. In various embodiments, the biodegradable polymer particle size, which may be in powdered form is from about 5 to 30 micrometers, however, in various embodiments ranges from about 1 micron to 300 microns may be used. In some embodiments, the at least one biodegradable polymer and the active pharmaceutical ingredient are the only components of the pharmaceutical formulation.

In some embodiments, at least 75% of the particles of the drug and the polymer have a size from about 10 micrometer to about 300 micrometers. In some embodiments, at least 85% of the particles have a size from about 10 micrometer to about 300 micrometers. In some embodiments, at least 95% of the particles have a size from about 10 micrometer to about 300 micrometers. In some embodiments, all of the particles have a size from about 10 micrometer to about 300 micrometers.

In some embodiments, at least 75% of the particles of the drug and the polymer have a size from about 20 micrometer to about 180 micrometers. In some embodiments, at least 85% of the particles have a size from about 20 micrometers to about 180 micrometers. In some embodiments, at least 95% of the particles have a size from about 20 micrometer to about 180 micrometers. In some embodiments, all of the particles have a size from about 20 micrometer to about 180 micrometers. In some embodiments, at least 80% of the particles have a size from 5 microns to about 100 microns on a volume basis.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method for preparing at least two polymers having a residual monomer content of less than 5%, the method comprising mixing the at least two polymers in a solvent to form a polymeric mixture, the at least two polymers having similar solubilities in the solvent, the polymeric mixture comprising at least one residual monomer and the polymeric mixture maintained at a pH in the range from 4-6, wherein the at least two polymers comprise a first polymer that is polylactide (PLA) and a second polymer that is polyglycolide (PGA) and wherein the polymeric mixture contains more PLA than PGA; and adding an antisolvent to the polymeric mixture so as to separate the at least two polymers from the polymeric mixture, the antisolvent maintained at a pH of about 7, wherein the residual monomer is soluble in the antisolvent and the at least two polymers are insoluble in the antisolvent.

2. A method according to claim 1, wherein the first polymer and the second polymer of the at least two polymers are added separately to and dissolved in the solvent to form a polymer blend in the mixture.

3. A method according to claim 1, wherein the separation of the at least two polymers further comprises at least decanting, centrifugation, microfiltration, ultrafiltration, sieving or a combination thereof the polymeric mixture to obtain the at least two polymers having low monomer content.

4. A method according to claim 1, further comprising drying the at least two polymers by evaporation with air or nitrogen or freeze-drying.

5. A method according to claim 1, wherein the polymeric mixture or the separated at least two polymers comprise at least three polymers and/or co-polymer blends.

6. A method according to claim 1, wherein the residual monomer content is from 0.1 to less than 5% w/w or v/v, and the at least two separated polymers have a particle size from about 5 micrometers to 500 micrometers.

7. A method according to claim 1, wherein (i) the solvent comprises n-hexane, cyclohexane, heptanes, methylene chloride, ethyl acetate, acetone or combinations thereof; or (ii) the antisolvent comprises water, ethanol, methanol, isopropyl alcohol, or mixtures thereof.

8. A method according to claim 1, wherein the polylactide content is at least 75% based on the total amount of polylactide and polyglycolide.

9. A method according to claim 1, wherein the monomer content of the at least two separated polymers is less than 0.1% w/w or v/v.

10. A method according to claim 1, wherein the polymeric mixture further comprises a dispersant comprising a gas or a surfactant.

11. A method according to claim 10, wherein the surfactant is an anionic, a cationic, an ampholitic, a non-ionic surfactant or a combination thereof.

12. A method according to claim 1, further comprising recovering the separated at least two polymers and forming a drug depot from the at least two recovered polymers by hot melt extrusion, co-extrusion, multi-layer extrusion, rotational molding, injection molding or casting.

13. A method for preparing at least two polymers having a residual monomer content of less than 5%, the method comprising adding an antisolvent to a mixture of at least two polymers dissolved in a solvent so as to precipitate the at least two polymers from the solvent, each of the at least two polymers having at least one residual monomer; wherein the residual monomer is soluble in the antisolvent, and wherein the precipitated polymers have a particle size from about 5 to about 30 micrometers.

14. A method according to claim 13, wherein a first polymer, a second polymer, and a third polymer of the at least two polymers are added separately to and dissolved in the solvent to form a polymer blend in the mixture.

15. A method for preparing at least two polymers according to claim 13, wherein the at least two polymers are removed from the solvent and anti-solvent so as to recover the at least two polymers having low residual monomer content of less than 0.5% v/v or w/w.

16. A method for reducing residual monomer content of at least two polymers in a mixture, the method comprising adding an anti-solvent to the mixture so as to precipitate the at least two polymers from the mixture, wherein the residual monomer is soluble in the antisolvent and the at least two polymers are insoluble in the antisolvent, wherein the at least two polymers are removed from the solvent and anti-solvent so as to recover the at least two mixed polymers having low residual monomer content of less than 1% w/w, and wherein the recovered polymers have a particle size from about 5 to about 30 micrometers.

17. A method according to claim 6, wherein the at least two separated polymers have a particle size from about 5 micrometers to 30 micrometers.

* * * * *

UNITED STATES PATENT AND TRADEMARK OFFICE
CERTIFICATE OF CORRECTION

PATENT NO.         : 9,242,004 B2
APPLICATION NO.    : 14/286673
DATED              : January 26, 2016
INVENTOR(S)        : Clay It is certified that error appears in the above-identified patent and that said Letters Patent is hereby corrected as shown below:

In the Specification

In Column 1, Line 9, delete "2012," and insert -- 2012, now Pat. No. 8,735,504, --, therefor.

In Column 11, Line 60, delete "2000 or" and insert -- 2000 µm, or --, therefor.

Signed and Sealed this
Twelfth Day of July, 2016

Michelle K. Lee
*Director of the United States Patent and Trademark Office*